United States Patent [19]

Naruse et al.

[11] Patent Number: 4,778,794
[45] Date of Patent: Oct. 18, 1988

[54] PHARMACEUTICAL COMPOSITION FOR THE TREATMENT OF INFANTILE AUTISM

[75] Inventors: Hiroshi Naruse, Tokyo; Masashi Takesada, Hyogo; Osamu Hayaishi; Yasuyoshi Watanabe, both of Kyoto, all of Japan

[73] Assignee: Suntory Limited, Osaka, Japan

[21] Appl. No.: 870,495

[22] Filed: Jun. 4, 1986

[30] Foreign Application Priority Data

Jun. 4, 1985 [JP] Japan .................................. 60-121347

[51] Int. Cl.$^4$ .................... A61K 31/50; A61K 31/495
[52] U.S. Cl. ................................................... 514/254
[58] Field of Search ......................................... 514/254

[56] References Cited

U.S. PATENT DOCUMENTS 4,665,182 5/1987 Nichol et al. ........................ 544/258
4,701,455 10/1987 Nichol et al. ........................ 544/258

Primary Examiner—Stanley J. Friedman
Attorney, Agent, or Firm—Cushman, Darby & Cushman

[57] ABSTRACT

A pharmaceutical composition for the treatment of infantile autism which contains tetrahydrobiopterin or a derivative thereof as a major effective ingredient and 5-hydroxytryptophan and/or L-DOPA as an optional auxiliary effective ingredient is provided.

5 Claims, 5 Drawing Sheets

2

PHARMACEUTICAL COMPOSITION FOR THE TREATMENT OF INFANTILE AUTISM

FIELD OF THE INVENTION

The present invention relates to a pharmaceutical composition for the treatment of infantile autism which contains tetrahydrobiopterin or a derivative thereof as an effective ingredient.

PRIOR ART

Ever since the finding of the dysfunctioning of the brain in autistic children, autism has been considered to be a disease caused by brain impairment. The etiology of autism has been ascribed to heredity, developmental anomaly or impairment at delivery but no lucid and convincing explanation has yet been put forward. Therefore, the treatments so far tried have been limited to nosotropic ones which involve the administration of such drugs as pimozide, haloperidol, pentoxyfylline and calcium hopantenate in accordance with the specific abnormal behaviors manifested by autistic patients, and no treatment which is truly etiotropic has been known [Acta paedopsychiat., 48, 173–184 (1982); Clin. Eval., 8, 629–673, December, 1980; Shinryo to Shinyaku (Diagnosis and New Drugs), 21, 4, Special Issue, Apr. 1, 1984).

Tetrahydrobiopterin and derivatives thereof are known compounds which have been used in the treatment of malignant hyperphenylalaninemia, depressions and Parkinson's disease (see, for example, Japanese Patent Public Disclosure Nos. 25323/1984 and 76086/1984).

As mentioned above, however, no etiotropic drug for the treatment of autism has been found and there exists a strong need to develop such a drug.

SUMMARY OF THE INVENTION

The present inventors obtained observations that indicate impaired cellular transport of aromatic amino acids in representative cases of children suffering from infantile autism. They therefore postulated that insufficiency of serotonin and catecholamines in the brain could cause autism and on the basis of this hypothesis, the inventors administered 5HTP (5-hydroxytryptophan) and L-DOPA (i.e., precursors for serotonin and catecholamines) to autistic children. In many cases, their symptoms were generally relieved but, in some cases, the symptoms were aggravated, probably because of overdosing of these drugs.

Therefore, instead of administering these two precursors, the present inventors used tetrahydrobiopterin which is a coenzyme for the hydroxylase of aromatic amino acids and which is a rate-limiting factor for the synthesis of serotonin and catecholamines. This compound turned out be surprisingly effective in the treatment of autism. The present invention has been accomplished on the basis of this finding.

DETAILED DESCRIPTION OF THE INVENTION

Figure 1:
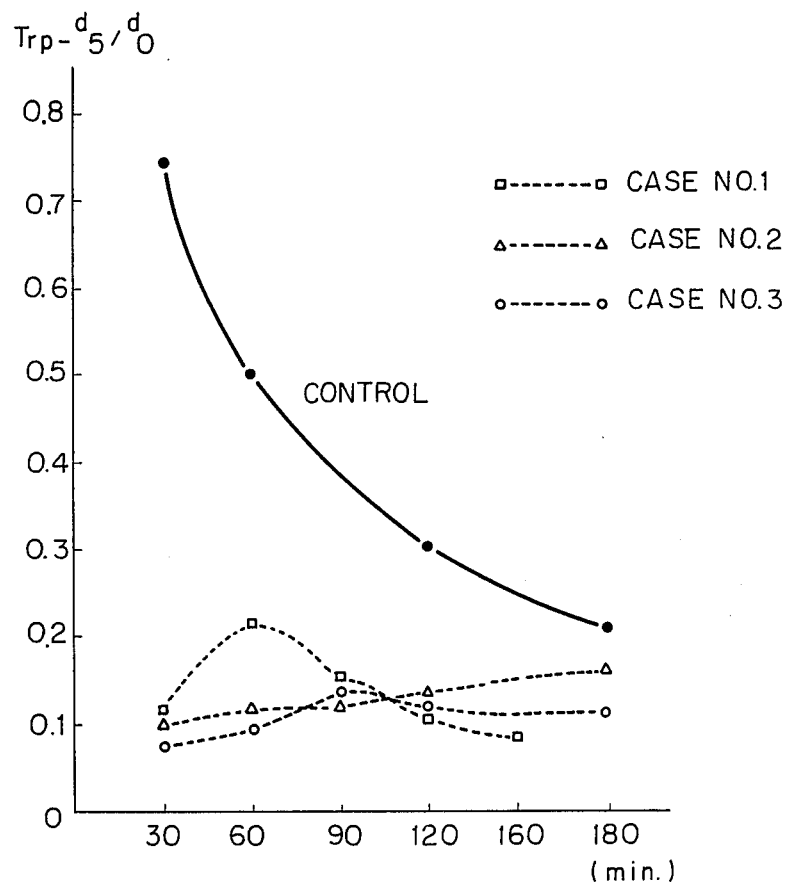
FIG. 1 is a graph depicting the blood level of Trp-$d_5$ as a function of time after it was administered per-orally to autistic children.

The present invention relates to a pharmaceutical composition for the treatment of autism which contains a compound of the formula (I):

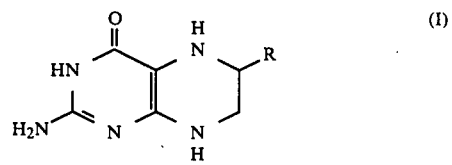

(wherein R is

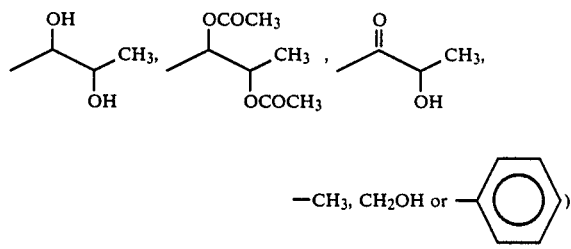

or a salt thereof as an effective ingredient.

Examples of an effective ingredient in the pharmaceutical composition of the present invention include the compounds listed below and salts thereof:

(1) L-erythro-5,6,7,8-tetrahydrobiopterin:

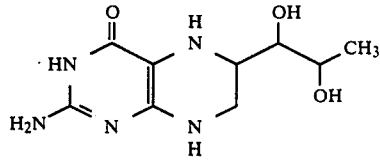

(2) DL-5,6,7,8-tetrahydrobiopterin:

(3) 1',2'-diacetyl-5,6,7,8-tetrahydrobiopterin:

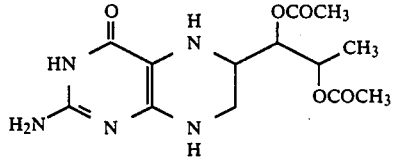

(4) sepiapterin:

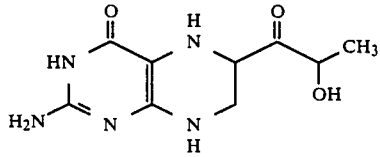

(5) 6-methyl-5,6,7,8-tetrahydropterin:

-continued

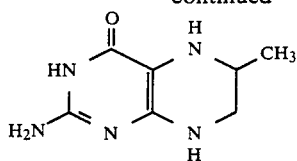

(6) 6-phenyl-5,6,7,8-tetrahydropterin:

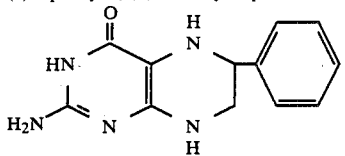

Among the compounds shown above, 5,6,7,8-tetrahydrobiopterin and salts thereof are preferable. In consideration of several factors such as toxicity, L-erythro-5,6,7,8-tetrahydrobiopterin and salts thereof are most preferable.

The compounds of formula (I) are known and are described in, for example, Japanese Patent Public Disclosure Nos. 25323/1984 and 76086/1984. Illustrative salts are those with pharmaceutically nontoxic acids such as hydrochloric acid, phosphoric acid, sulfuric acid, boric acid, acetic acid and formic acid. Salts of the compounds of formula (I) with such acids are also included in the definition of the "active ingredient" in the pharmaceutical composition of the present invention.

The pharmaceutical compositions of the present invention may be prepared by formulating them in dosage forms which are suitable for peroral, rectal or nonparenteral administration, the last-mentioned including intravenous injection and administration into the cerebrospinal fluid. For this purpose, common carriers and routine formulation techniques may be employed.

"Common carriers" means those which are employed in standard pharmaceutical preparations and includes excipients, binders and disintegrators the choice of which depends on the specific dosage form used. Typical examples of the excipient are starch, lactose, sucrose, glucose, mannitol and cellulose; illustrative binders are polyvinylpyrrolidone, starch, sucrose, hydroxypropyl cellulose and gum arabic; illustrative disintegrators include starch, agar, gelatin powder, cellulose, and CMC. Any other common excipients, binders and disintegrators may also be employed.

In addition of the carriers described above, the pharmaceutical composition of the present invention preferably contains antioxidants for the purpose of stabilizing the effective ingredient. Appropriate antioxidants may be selected from among those which are commonly incorporated in pharmacueticals and include ascorbic acid, N-acetylcystein, L-cystein, dl-α-tocopherol, and natural tocopherol. These antioxidants are preferably used in amounts that stabilize the active compound and the weight ratio of the antioxidant to the active compound generally ranges from 0.2 to 1.5.

Formulations of the pharmaceutical composition of the present invention which are suitable for peroral administration may be provided in the form of tablets, capsules, powders, granules, or suspensions in nonaqueous solutions such as syrups, emulsions or drafts, each containing one or more of the active compounds in predetermined amounts.

The granule may be provided by first preparing an intimate mixture of one or more of the active ingredients with one or more of the auxiliary components shown above, then granulating the mixture, and classifying the granules by screening through a sieve.

The tablet may be prepared by compressing or otherwise forming one or more of the active ingredients, optionally with one or more auxiliary components.

The capsule may be prepared by first making a powder or granules as an intimate mixture of one or more of the active ingredients with one or more auxiliary components, then charging the mixture into an appropriate capsule on a packing machine, etc.

The pharmaceutical composition of the present invention may be formulated as a suppository (for rectal administration) with the aid of a common carrier such a cocoa butter.

The pharmaceutical composition of the present invention may also be formulated in a dosage form suitable for non-parenteral administration by packaging one or more active ingredients as dry solids in a sterile nitrogenpurged container. The resulting dry formulation may be administered to patients non-parenterally after being dispersed or dissolved in a given amount of aseptic water.

The dosage forms are preferably prepared from a mixture of the active ingredients, routine auxiliary components and one or more of the antioxidants listed above. If desired, the formulations may further contain one or more auxiliary components selected from among excipients, buffers, flavoring agents, binders, surfactants, thickening agents, and lubricants.

The dose of the active compound of formula (I) will of course vary with the route of administration, the severity of the disease to be treated, and the patient to be treated, but the exact dose ultimately chosen should be left to the good discretion of the doctor responsible for the treatment.

A dose whichis appropriate for the treatment of autistic disorders generally ranges from 0.1 to 50 mg/kg body weight/day, and a typical effective dose is within the range of 0.5 to 10 mg/kg body weight/day.

If a desired dose is determined, the active ingredient may be administered once a day or, alternatively, it may be administered in up to four portions daily at suitable intervals.

The active ingredient may be straightforwardly administered without being mixed with any other components. However, for several reasons, typically for the purpose of providing ease in controlling the dose level, the active compound is preferably administered in a pharmaceutical dosage form.

In addition to the compound of formula (I), the dosage formulation of the pharmaceutical composition of the present invention may contain 5-hydroxytryptophan (5HTP) and/or L-dopa (L-DOPA) as an auxiliary active ingredient. It has been observed that the combined use of these active ingredients proves even more effective in treating autism than when the active ingredient of formula (I) is used alone. If two or more active ingredients are used, their proportions are not limited to any particular value but, as guide figures, 5HTP and/or L-DOPA may be used in amounts, on a weight basis, of 0.1 to 10, preferably 0.5 to 2 parts, per 1 part of the active ingredient of formula (I).

If a pharmaceutical composition containing the mixture of active compound (I) and 5HTP and/or L-DOPA is used in treatment of autism, an appropriate dose is such that the sum of the active ingredients ranges from 0.1 to 50 mg/kg body weight/day, preferably from 0.5 to 10 mg/kg body weight/day.

Whether the patient should be treated with a preparation containing the compound of formula (I) as the sole active ingredient or with a preparation containing both the compound (I) and 5HTP and/or L-DOPA will be decided by the good judgement of the doctor depending upon the patients age and or the severity of the disease.

As already mentioned, the active compounds which are most preferable for use in the treatment of autism are optically active L-erythro-5,6,7,8-tetrahydrobiopterin and salts thereof. They may be replaced by analogues thereof, such as DL-tetrahydrobiopterin, 1',2'-diacetyltetrahydrobiopterin, sepiapterin, 6-methyl-5,6,7,8-tetrahydropterin, 6-phenyl-5,6,7,8-tetrahydropterin, and salts thereof. It should, however, be emphasized again that from the viewpoints of nontoxicity and other factors, L-erythro-5,6,7,8-tetrahydrobiopterin which exists in vivo is most preferable. It will be interesting to note that the acute toxicity of the L-erythro-5,6,7,8-tetrahydrobiopterin dihydrochloride which was administered to rats per-orally was 2 g/kg or more, indicating the substantial absence of toxicity in this compound. The non-optically active form, DL-tetrahydrobiopterin, also presents low toxicity as demonstrated in the treatment of Parkinson's disease in Japanese Patent Public Disclosure Nos. 76086/1984 and 25323/1984, and may be used for the treatment of autism. Little acute toxicity is also found in the other compounds represented by the formula (I).

The following examples are provided for the purpose of further illustrating the present invention but are in no sense to be taken as limiting.

EXAMPLE 1

(Granules)

One part of polyvinylpyrrolidone (Kollidon 30) was dissolved in sterile purified water. The solution was uniformly mixed with 10 parts of ascorbic acid and 5 parts of L-cysteine hydrochloride. Thereafter, 10 parts of tetrahydrobiopterin dihydrochloride was added and a uniform mixture was obtained.

The resulting solution was added to 59 parts of an excipient (mannitol or lactose) and 15 parts of a disintegrator [corn starch or hydroxypropyl cellulose (LH-22)] and the kneaded mixture was granulated, dried and sieved.

EXAMPLE 2

(Tablets)

A uniform solution of tetrahydrobiopterin was prepared as in Example 1 and mixed with 58 parts of lactose and 15 parts of microcrystalline cellulose. To the mixture, one part of magnesium stearate was added and the resulting mixture was pelletized to form tablets.

EXAMPLE 3

(Capsules)

Granules as prepared in Example 1 were charged into capsules, with 0.2% magnesium stearate incorporated as a lubricant.

EXAMPLE 4

(Injection)

| Tetrahydrobiopterin dihydrochloride | 1.5 g |
| --- | --- |
| Ascorbic acid | 1.5 g |
| L-cysteine hydrochloride | 0.5 g |
| Mannitol | 6.5 g |

The above-listed components were dissolved in sterile purified water to make a volume of 100 ml. The solution was sterilized by filtration, put into vials or ampules in 1- or 2-ml portions, freeze-dried and the containers sealed.

EXAMPLE 5

(Injection)

Tetrahydrobiopterin dihydrochloride (2.0 g) was dissolved in sterile purified water in an oxygen-free atmosphere to make a volume of 100 ml. The solution was sterilized by filtration, worked up as in Example 4, and the container sealed.

EXAMPLE 6

(Suppository)

| Tetrahydrobiopterin dihydrochloride | 150 parts |
| --- | --- |
| Ascorbic acid | 150 parts |
| L-cysteine hydrochloride | 50 parts |

A uniform powder prepared from these components was dispersed in 9,950 parts of cocoa butter.

EXAMPLE 7

(Granules)

| Tetrahydrobiopterin dihydrochloride | 5 parts |
| --- | --- |
| Ascorbic acid | 5 parts |
| L-cysteine hydrochloride | 2 parts |

A uniform solution was prepared from these components, and added to a uniform mixture of mannitol (55 parts), polyvinylpyrrolidone (1 part), hydroxypropyl cellulose (14 parts) and 5-hydroxytryptophan (5 parts). The kneaded mixture was granulated, dried and sieved.

EXAMPLE 8

(Granules)

| Tetrahydrobiopterin dihydrochloride | 5 parts |
| --- | --- |
| Ascorbic acid | 5 parts |
| L-cysteine hydrochloride | 5 parts |
| Mannitol | 52 parts |
| Polyvinylpyrrolidone (Kollidon 30) | 1 part |
| Hydroxypropyl cellulose (LH-22) | 12 parts |
| L-DOPA | 10 parts |

These components were worked up as in Example 7, followed by granulation and sieving, except that 5 parts of 5-hydroxytryptophan was replaced by 10 parts of L-DOPA.

EXAMPLE 9

(Granules)

| Tetrahydrobiopterin dihydrochloride | 5 parts |
|---|---|
| Ascorbic acid | 5 parts |
| L-cysteine hydrochloride | 2 parts |

A uniform solution was prepared from these components, and added to a uniform mixture of 5-hydroxy-tryptophan (5 parts), L-DOPA (10 parts), mannitol (50 parts), polyvinylpyrrolidone (Kollidon 30) (1 part) and hydroxypropyl cellulose (LH-22) (9 parts). The kneaded mixture was granulated, dried and sieved.

The definition of autism and the legitimacy of its treatment with tetrahydrobiopterin based on biochemical observations are discussed below.

DEFINITION AND DIAGNOSIS OF AUTISM

The WHO defines infantile autism as follows: (1) it is a syndrome manifested within 30 months of birth; (2) it involves abnormal responses to visual and auditory stimulations (such as impaired understanding of language, retarded development of language, and bizarre echolalia); (3) it involves impaired social and interpersonal relations; and (4) it involves frequent stereotyped or manneristic behaviors. Patients to be treated by tetrahydrobiopterin were selected by examination to check whether their symptoms satisfied the WHO's definition of autism. Clinical symptoms and changes in abnormal behaviors were evaluated by the "Rating Scale for Abnormal Behaviors in Children" and "Children's Behavior Checklist" prepared by the "Study Group on Behavioral Disorders in Children".

RESULTS OF BIOCHEMICAL STUDIES OF AUTISM

Figure 2:
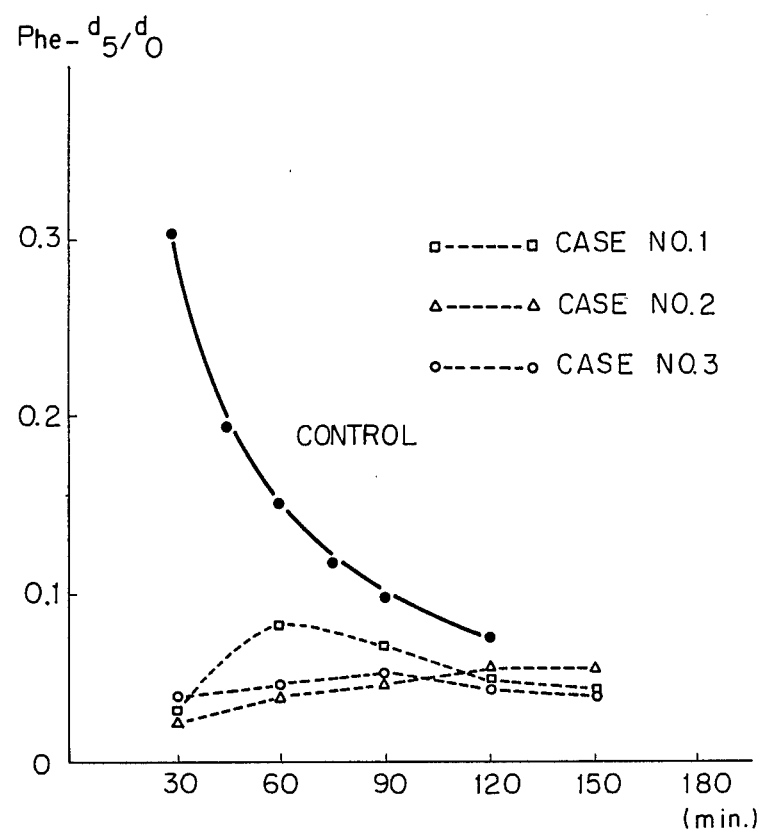
FIG. 2 is a graph showing the blood level of Phe-$d_5$ as a function of time after it was administered pre-orally to autistic children.
Figure 3:
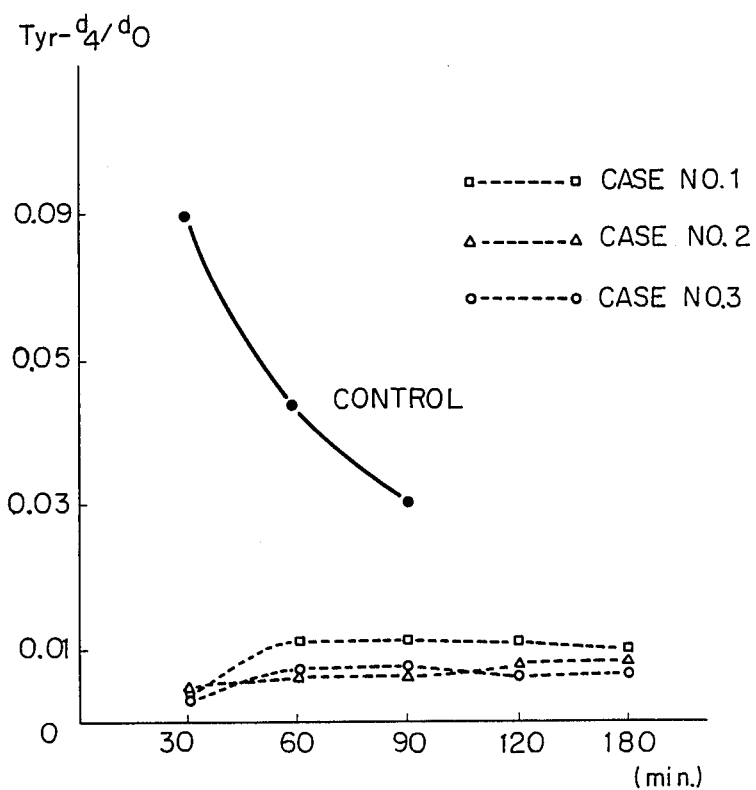
FIG. 3 is a graph showing the blood level of Tyr-$d_4$ as a function of time after it was administered pre-orally to autistic children.

Children with infantile autism who were selected on the basis of examination in consideration of the WHO's definition were given perorally deuterated-phenylalanine (labelled on the aromatic ring and hereinafter abbreviated as Phe-$d_5$) and deuterated tryptophan (labelled on the indole nucleus and hereinafter abbreviated as Trp-$d_5$). The results of analyses of Phe-$d_5$, Trp-$d_5$ and Tyr-$d_4$ (deuterated tyrosine produced as a result of metabolization of Phe-$d_5$ and labelled on the aromatic ring) in blood are shown in FIGS. 1 to 3, from which one can clearly see impaired transport of Trp-$d_5$ and Tyr-$d_4$ into the blood. The data in FIGS. 1 and 2 show impaired uptake of Trp-$d_5$ and Phe-$d_5$, and the Tyr-$d_4$ disappearance curve in FIG. 3 differs entirely from the normal curve. These results suggest that infantile autism involves abnormal transport of aromatic amino acids, and this phenomenon exist not only between blood and the intestines but also between blood and the brain. Impaired uptake of aromatic amino acids would reduce the supply of amino acids into the brain, which may lead to chronic insufficiency of serotonin and catecholamines in the brain. In the formation of serotonin, the tryptophan level could be an enzymatic activity limiting factor.

On the other hand, high blood serotonin levels in autistic children have been reported and the present inventors have confirmed that this is an indisputable fact. However, when deuterated tryptophan-3-3-$d_2$ (hereunder abbreviated as Trp-$d_2$) was administered to rats either perorally or by intraperitoneal injection, a large amount of deuterated serotonin (hereunder 5HT-$d_2$) was detected in the brain 30 minutes later whereas no detectable amount of 5HT-$d_2$ was found in the other organs checked, the only exception being the intestinal tract where a very small amount of 5HT-$d_2$ was detected. This indicates that although serotonin synthesis in the brain is very rapid, it is not synthesized in either platelets or plasma in the blood until several hours have passed from the administration of Trp-$d_2$ Clinical observations of hish serotonin levels in autistic children would be explained as follows: impaired absorption of tryptophan by the intestinal tract causes excessive, although gradual, synthesis of serotonin in that location, from which excess serotonin is taken up by platelets. It is therefore postulated that high serotonin levels in the blood do not necessarily mean high serotonin levels in the brain, and that the reported assumption of high serotonin levels in the brain of autistic patients is quite dubious.

Therefore, on the basis of the hypothesis that the levels of serotonin and catecholamines decrease in the brain of autistic patients, the present inventors administered very small amounts of 5HTP (5-hydroxytryptophan) and L-DOPA, precursors of these amines, to the patients. The results were remarkable but the administration of these precursors required very strict dose control since any overdosage aggravated the symptoms of the patients because of the irritating action of the drugs.

The present inventors therefore reached the idea that better results would be obtained if, in addition to these amine precursors which regulate the levels of serotonin and catecholamines in the brain, tetrahydrobiopterin which is a coenzyme that is involved in the biosynthesis of these amines as their regulators was administere. The therapeutic effects of this coenzme, optionally in combination with 5HTP and/or L-DOPA, were remarkable as demonstrated in the following case studies.

Case 1: 6-year-old boy

The patient would not laugh at all and this symptom emerged about 10 months after his birth. He avoided eye contact and entirely lacked verbosity, two typical symptoms of autism. An interview with the patient revealed that he was abnormal with respect to 23 out of the 24 items in Checklist for the History of Abnormal Behaviors prepared by the "Study Group on Behavioral Disorders in Children". The patient was six years and one month old when he was brought to Musashi National Nursing Home, Tokyo, Japan. Among the most noticeable of his symptoms were: hyperkinesis, inability to interact with other people, echolaria, delayed echolaria, inability to make communicative speech, inability to verbalize, animal noise, sloppiness, and attachment to certain objects. The patient was not able to get along with classmates. Pimozide, pentoxyphylline and calcium hopantenate were either ineffective or their continued administration was impossible. His symptoms were not relieved by administration of 10 mg/kg of L-DOPA; on the contrary, this drug aggravated the patients symptoms and, hence, its application was discontinued.

Starting six weeds after the administration of L-DOPA was discontinued, 5HTP was administered at a dose of 1 mg/kg/day. Eight weeks after the commencement of 5HTP administration, the frequency of echolalia decreased and the patient started to utter normal words and sentences. In the ninth week, 2 mg/kg of L-DOPA was administered in addition to 5HTP; the patient acquired the ability to lead a school life and interact with other children but no further improvements were attained. Therefore, the administration of L-erythro-5,6,7,8-tetrahydrobiopterin (hereunder BPH₄) was incorporated in the regimen.

When 2.5 mg/kg/day of BPH₄ was administered in addition to 5HTP and L-DOPA, the patient got excited for a while but at day he became less excitable, and thereafter, he was well disciplined and could play with other children. One week later, the administration of 5HTP and L-DOPA was discontinued and only BPH₄ was given at a dose of 2.5 mg/kg/day, but the symptoms of the patients were further relieved.

One week after the administration of BPH₄ alone, 5HTP (1 mg/kg/day) was again administered in combination with 1 mg/kg/day of BPH₄. After one week of the combined administration of BPH₄ and 5HTP, the patient became normal in terms of understanding instructions, playing, sleeping and interacting with his family. He even became able to attend school, walk alone, and go out of his home in the same way as normal children. In view of such pronounced improvements, the administration of BPH₄ was discontinued at week 6 and only 5HTP was administered thereafter. Then, the patient feel again into hyperkinesis, requently uttered animal noises, and refused to stop this undesirable behavior when ordered to do so verbally. His symptoms were further aggravated when the administration fo 5HTP was suspended.

Figure 4:
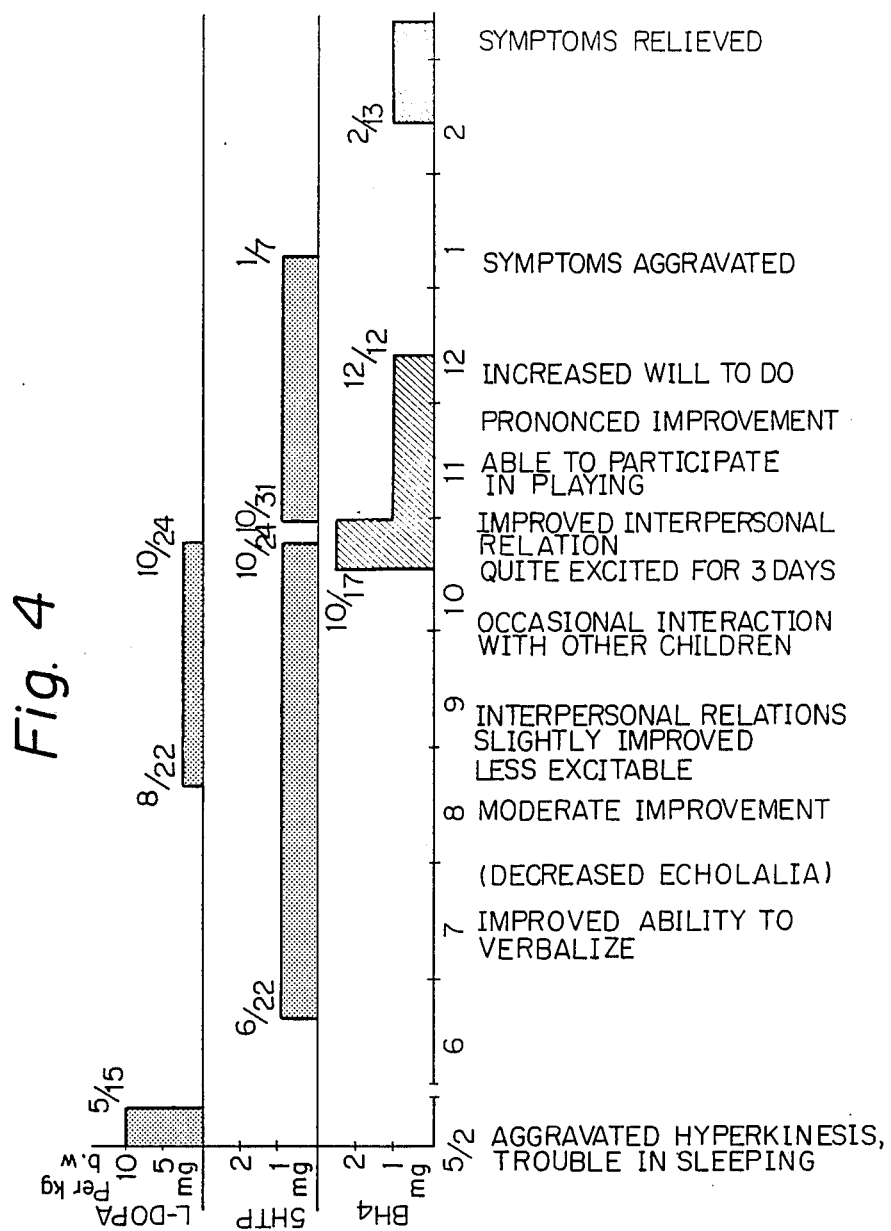
FIGS. 4 and 5 are charts which outline the time schedule of administration of BPH$_4$, 5HTP and L-DOPA and the resulting changes in the symptoms of Cases 1 and 2, respectively.

Following a suspension of about 8 weeks in the administration of drugs, the administration fo BPH₄ above (1 mg/kg/day) was resumed. The patient still suffered from hyperkinesis and would laugh to himself. However, his ability to understand language improved and he became able to interact and converse with others people, making appropriate responses to them (FIG. 4 and Table 1).

years and 8 months old, the patient was unable to speak, did not obey verbal instructions, was hyperactive lacked outward expressiveness, and showed abnormal attachment to objects. Pimozide, pentoxyphylline and calcium hopantenate were ineffective. The patient was five years old when he was hospitalized at Municipal Children's Health Center, Osaka, Japan.

The patient was given L-DOPA at a dose of 10 mg/kg/day. At day 10, he showed increasing interest in other people and manifested other responses which were, however, by no means pronounced.

At day 11 and afterward, both 5HTP (1 mg/kg/day) and L-DOPA (10 mg/kg/day) were administered. About two weeks after this combined drug regimen, the patient started to respond to other person's calls and to verbalize his feelings. However, the improvement was not appreciable and the drug treatment was suspended after four weeks.

In the fifth week and afterward, the patient was given BPH₄ (1 mg/kg/day) alone. The patient's interpersonal transactional mode improved and he responded to selected persons, enabling others to infer his emotions. He expressed his emotions with words and he showed increasing interest in exercising the whole body and playing ball. The overall improvement was pronounced.

In the seventh week and afterward, the patient was given both BPH₄ (1 mg/kg/day) and 5HTP (1 mg/kg/day). He showed better understanding of language and became able to develop a social life with other children. He also learned to count numbers and be patient. The improvements were great.

When the drug application was discontinued in the 12th week, the patient gradually post his patience, got easily excited and showed a tendency to avoid eye contact. During a 10-day intermission, the symptoms of the patient became seriously aggravated.

After the 10-day intermission, the administration of

TABLE 1

| | Changes in Symptoms of Case 1 at Various Stages of Drug Administration | | | | | | | | |
|---|---|---|---|---|---|---|---|---|---|
| | Before Treatment | L-DOPA (10) | 5HTP (2) | 5HTP (1) + L-DOPA (2) | BH₄ (2.5) + 5HTP (1) + L-DOPA (2) | BH₄ (2.5) | BH₄ (1) + 5HTP (1) | 5HTP (2) | BH₄ (1) |
| Hyperkinesis | +++ | +++ | ++ | ++ | +++ | ++ | ± | ++ | + |
| Emotional Lability | +++ | +++ | ++ | ++ | ++ | ++ | + | + | + |
| Attachment | +++ | +++ | +~++ | +~++ | +~++ | +~++ | + | ++ | + |
| Refusal | ++ | ++ | + | + | + | + | + | ++ | + |
| Poor verbalization | ++ | ++ | + | + | +~++ | + | ± | ++ | + |
| Echolaria | +++ | +++ | + | + | + | + | ± | ++ | ± |
| Poor understanding | ++ | ++ | + | + | + | + | ± | ++ | + |
| Lack of communication | +++ | +++ | ++ | + | + | + | + | +~++ | + |
| Inability to play | +++ | +++ | ++ | + | + | ± | ± | + | ± |
| Poor adaptability | +++ | +++ | ++ | + | + | ± | ± | + | + |
| Stereotyped behavior | ++ | ++ | + | + | ++ | +~++ | + | +~++ | + |
| Insistence on the preservation of sameness | +++ | +++ | + | + | + | + | + | +~++ | + |
| Trouble in sleeping | + | +++ | ± | +~++ | +~++ | ± | — | + | — |
| Rating of improvement | | aggravated | slightly improved | improved | slightly aggravated | improved | markedly improved | aggravated | improved |

+++: abnormalities very pronounced;
++: abnormalities pronounced;
+: abnormalities slight;
—: abnormalities unnoticeable Case 2: 5-year-old boy Since earliest infancy, the patient manifested such symptoms as the avoidance of eye and human contact. Interview with the patient revealed that he was abnormal with respect to 22 out of the 24 items in the Children Behavior Checklist prepared by the "Study Group on Behavioral Disorders in Children". When he was 4

Figure 5:
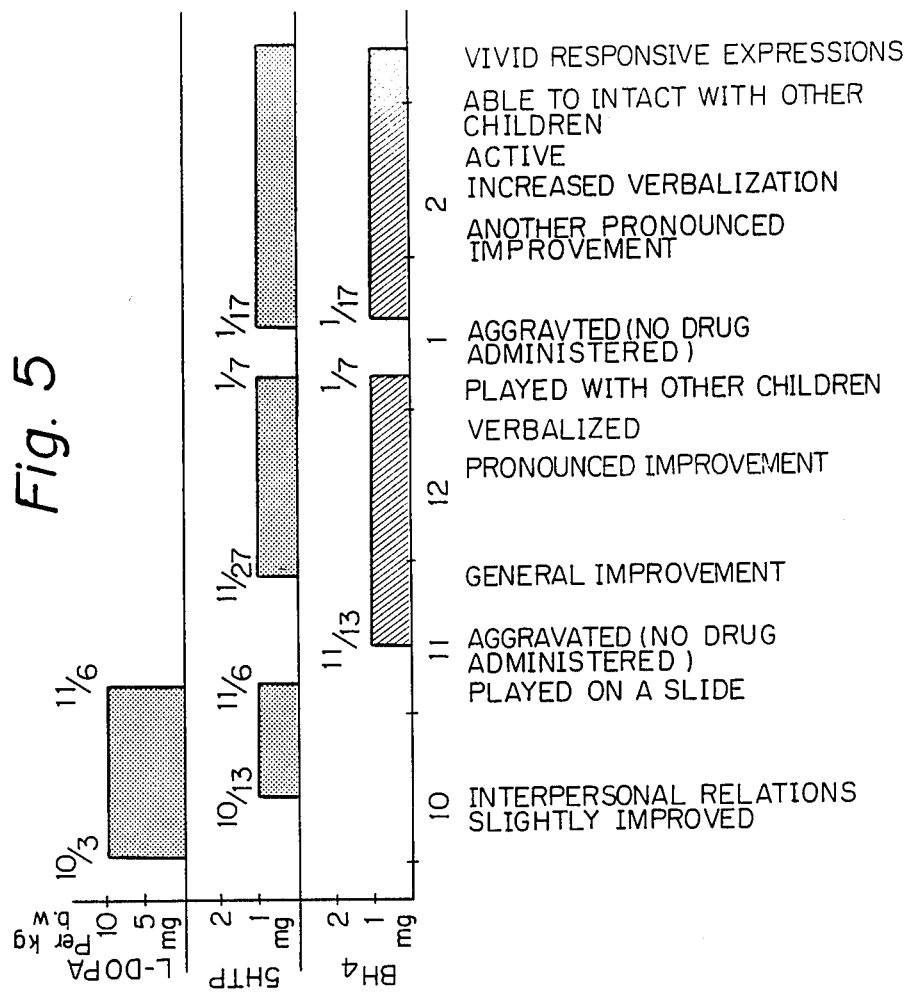

BPH₄ (1 mg/kg/day) and 5HTP (1 mg/kg/day) was resumed. The improvement in the patient's ability to understand language, interact with other people, and respond to other person's calls was so remarkable that the patient almost looked like a normal child (FIG. 5 and Table 2).

TABLE 2

Changes in Symptoms of Case 2 at Various Stages of Drug Administration

| | Before Treatment | L-DOPA (10) | 5HTP (1) + L-DOPA (10) | BH4 (1) | BH4 (1) + 5HTP (1) | After Intermission | BH4 (1) + 5HTP (1) |
|---|---|---|---|---|---|---|---|
| Hyperkinesis | ++ | ++ | + | + | ± | + | − |
| Emotional Lability | +++ | + | ± | ± | ± | ++ | ± |
| Attachment | +++ | ++ | ++~+ | + | + | + | + |
| Refusal | +++ | ++ | + | − | − | + | − |
| Poor verbalization | +++ | +++ | +++ | + | + | ++ | + |
| Echolaria | | | | + | + | + | ± |
| Poor understanding | +++ | ++ | + | ± | ± | + | ± |
| Lack of communication | +++ | + | + | ± | ± | ++ | ± |
| Inability to play | +++ | ++ | + | + | ± | + | ± |
| Poor adaptability | +++ | + | + | + | ± | + | ± |
| Stereotyped behavior | +++ | +++ | ++ | + | + | + | ± |
| Insistence on the preservation of sameness | +++ | +++ | ++ | + | + | + | ± |
| Trouble in sleeping | + | + | − | − | − | − | − |
| Rating of improvement | | slightly improved | improved | markedly improved | drastically improved | aggravated | drastically improved |

+++: abnormalities very pronounced;
++: abnormalities pronounced;
+: abnormalities slight;
−: abnormalities unnoticeable The above-described cases are totally representative of autistic patients and were objectively supported by the Checklist of Medical History and the "Rating Scale for Present Abnormal Behaviors in Children" prepared by the "Study Group on Behavioral Disorders in Children". The present inventors administered BPH4 to these representative cases and attained strikingly good results. The ability of BPH4 to alleviate the symptoms of autism was also demonstrated by the fact that the patients got worse as a result of discontinuation of drug treatment and that they changed for better when drug administration was resumed.

Remarkable effects were attained even when BPH4 was administered alone, but the two case studies demonstrate that satisfactory results could also be obtained by using BPH4 in combination with 5HTP and/or with L-DOPA capable of increasing the levels of catecholamines in the brain.

We claim:

1. A method for ameliorating disorder of infantile autism, wherein an autistic child receives a pharmaceutical composition comprising a compound of the formula:

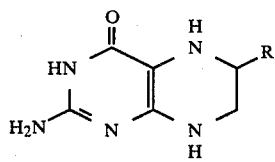

(wherein R is

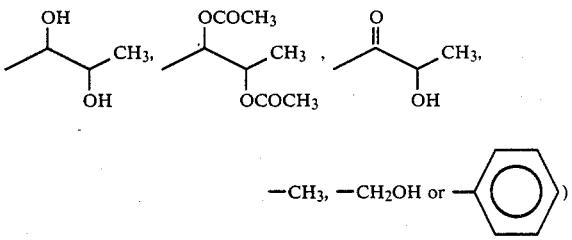

or a salt thereof as an effective ingredient, at a dose wherein the amount of the effective ingredient received is in the range of 0.1 to 50 mg/kg body weight/day together with a pharmaceutically acceptable carrier.

2. A method according to claim 1, wherein the pharmaceutical composition further contains an anti-oxydizing agent selected from the group comprising ascorbic acid, N-acetylcysteine, L-cysteine, dl-α-tocopherol and natural tocopherol.

3. A method according to claim 1, wherein the amount of the effective ingredient received is in the range of 0.5 to 10 mg/kg body weight/day.

4. A method according to claim 1, wherein R is

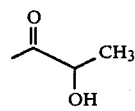

5. A method according to claim 1, wherein the effective ingredient is L-erythro-5,6,7,8-tetrahydrobiopterin.